(12) United States Patent
Chen et al.

(10) Patent No.: US 7,575,764 B2
(45) Date of Patent: Aug. 18, 2009

(54) **COMPOSITIONS COMPRISING *HYPSIZYGUS ULMARIUS* EXTRACT**

(75) Inventors: Chia Chen, New Rochelle, NY (US); Andrew Weil, Vail, AZ (US); Paul Stamets, Shelton, WA (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 11/536,885

(22) Filed: Sep. 29, 2006

(65) Prior Publication Data

US 2008/0286298 A1    Nov. 20, 2008

Related U.S. Application Data

(60) Provisional application No. 60/722,631, filed on Oct. 1, 2005.

(51) Int. Cl.
*A01N 65/00* (2006.01)
*A61K 36/268* (2006.01)
*A61K 36/906* (2006.01)

(52) U.S. Cl. .................. 424/725; 514/886; 424/756
(58) Field of Classification Search .............. None
See application file for complete search history.

(56) References Cited

U.S. PATENT DOCUMENTS

| | | | |
|---|---|---|---|
| 5,235,064 A | 8/1993 | Gapinski | |
| 6,682,763 B2 * | 1/2004 | Kuno et al. | 424/769 |
| 6,864,251 B2 | 3/2005 | Kucharik et al. | |
| 2002/0013368 A1 | 1/2002 | Collin et al. | |
| 2004/0091863 A1 | 5/2004 | Ramakrishnan | |
| 2006/0018867 A1 * | 1/2006 | Kawasaki et al. | 424/70.122 |
| 2006/0045887 A1 * | 3/2006 | Mahajna et al. | 424/195.15 |

FOREIGN PATENT DOCUMENTS

| | | |
|---|---|---|
| DE | 10151649 | 5/2003 |
| JP | 63-183537 | 7/1988 |
| JP | 04-247009 | 9/1992 |
| JP | 05-306233 | 11/1993 |
| JP | 11-228439 | 8/1999 |
| JP | 11-292785 | 10/1999 |
| JP | 2003306422 A * | 10/2003 |
| KR | 2004084581 | 10/2004 |
| WO | WO2005/067955 | 7/2005 |

OTHER PUBLICATIONS

Camp et al; Production of Intraderma Microabscesses by Topical Application of Leukotriene B4; Journal of Investigative Dermatology; vol. 82(2) pp. 202-204, 1984.
Lombardi et al; Mycological Medicine; Functional Foods & Nutraceuticals; Jan. 2002.
Roundtree, R.; Mycological Medicine: Peer Review Notes; Functional Foods & Nutraceuticals; Jan. 2002.
Hsu et al; Signaling mechanisms of enhanced neutrophil phagocytosis and chemotaxis by . . . *Ganoderma lucidum*; British journal of Pharmacology; vol. 139(2); pp. 289-298, 2003.
Zhu et al.; The Scientific Rediscovery of a Precious Ancient Chinese Herbal Regimen: *Cordyceps sinensis* Part II; Journal of ACM; vol. 4(4), 1998 pp. 429-457.
Stamets, P.; Novel Antimicrobial from Mushrooms; HerbalGram; vol. 54, 2002; pp. 28-33.
Douglas et al; Why does inflammation persist a dominant role for the stromal microenvironment?; Expert Reviwes in Molecular Medicine; Cambridge University Press; Dec. 9, 2002.
Henderson, W.; The Role of Leukotrienes in Inflamation; Annals of Internal Medicine; vol. 121(9); Nov. 1, 1994; pp. 684-697.
D'Amelio, F.; Botanicals: A Phytocosmetic Desk Reference; CRC Press; 1999; p. 181.

* cited by examiner

*Primary Examiner*—Michele Flood
*Assistant Examiner*—Qiuwen Mi
(74) *Attorney, Agent, or Firm*—Peter Giancana

(57) ABSTRACT

Disclosed are topical compositions comprising extracts of *Hypsizygus ulmarius* in amounts that are effective to influence LTB4-mediated chemotaxis and/or IL-1β mediated adhesion of polymorphonuclear leukocytes. The *hypsizygus ulmarius* extract may be used alone or in combination with secondary anti-inflammatory and skin active agents, such as other mushroom and/or natural extracts. The secondary anti-inflammatory agents may or may not function by antagonizing LTB4-mediated chemotaxis and IL-1β mediated adhesion. The extract may be incorporated into a cosmetically acceptable vehicle. The present invention includes methods of treating skin inflammation by applying to inflamed skin, anti-inflammatory effective amounts of *Hypsizygus ulmarius* extract in a defined treatment regimen.

8 Claims, No Drawings

COMPOSITIONS COMPRISING *HYPSIZYGUS ULMARIUS* EXTRACT

This application claims priority from provisional application 60/722,631, filed Oct. 1, 2005.

FIELD OF THE INVENTION

The present invention pertains to the fields of cosmetics and dermatology, specifically to topical anti-inflammatory compositions comprising extracts of mushroom.

BACKGROUND

The natural response of healthy human tissue to damage or attack is inflammation. The tissues of the human body may come under attack or otherwise be compromised by a variety of factors, including microbial infection, non-living foreign matter, ionizing radiation and oxidative stress. Under the right conditions, inflammation may be present in virtually all tissue types in the human body, including the major organs (heart, brain, liver, kidneys, etc) and the skin. By "oxidative stress" we mean unwanted changes in animal tissues that are caused by reactive oxygen species (pro-oxidants) present within the tissue. Oxidative stress develops through an imbalance wherein the effects of pro-oxidants dominate over the effects of anti-oxidants. Examples of pro-oxidants that accumulate in human tissues include oxygen ions, free radicals and peroxides, for example, superoxide and hydrogen peroxide. Reactive oxygen species result from normal cell metabolism, but under balanced conditions their destructive effects are checked by anti-oxidants in the organism. Examples of such anti-oxidants are superoxide dismutase and catalase.

Leukotriene B4

Helpful for developing an appreciation of the present invention is an understanding of the synthesis and role of leukotriene LTB4, a potent pro-inflammatory agent. Following an inflammatory stimulus, a first step in a complex cascade of reactions is an influx of calcium ions into certain cells. These cells may include neutrophils, eosinophils, monocytes, macrophages, mast cells, basophils and B lymphocytes. Within these cells, the influxing calcium ions and ATP bind to inactive 5-lipoxygenase and this leads to the translocation of 5-lipoxygenase out of the cytosol and into the cell membrane, where it anchors to 5-lipoxygenase activating protein (FLAP). The calcium ion influx also prompts the translocation of phospholipase A2 from the cytosol to the cell membrane, where it cleaves an arachidonic acid glycerol ester. The arachidonic acid glycerol ester is a naturally occurring phospholipid component of the cell membrane and when cleaved by phospholipase A2, it releases arachidonic acid, an unsaturated fatty acid, into the cytosol. Other mechanisms of arachidonic acid release into the cytosol include the action of certain cytokines, namely, tumor necrosis factor (TNF) and interleukin-1 (IL1). Regardless, a freed arachidonic acid molecule binds to a translocated 5-lipoxygenase molecule and is converted into 5-hydroperoxyeicosatetraenoic acid (5-HPETE). 5-HPETE is in turn acted upon by a cytosolic 5-lipoxygenase molecule to form leukotriene A4 (LTA4), which is then released into the cytosol. Some LTA4 may be secreted by the cell while some LTA4 remains in the cell and is hydrolyzed into leukotriene B4 (LTB4) under the action of LTA4 hydrolase. The secreted LTA4 may be taken up by cells that do not produce LTA4 themselves, but which are otherwise capable of converting LTA4 into LTB4. These cells may be thought of as a secondary sources of LTB4. Once produced in either primary or secondary cells, LTB4 passes through the cell membrane into the extracellular environment. The secreted LTB4 initiates a number of cellular and molecular actions that direct, as well as amplify, the inflammatory process. LTB4 has a number of functionalities that allow it to direct this stage of the inflammatory process. Broadly, LTB4 has chemotactic, chemokinetic, vasoactive, pain mediating, immuno-modulating and other properties. It also stimulates degranulation and production of superoxide within leukocytes.

Following its secretion, LTB4 attracts to the affected site, neutrophils circulating in the blood. LTB4 is the a potent chemotactic agent for neutrophils that express the appropriate chemoattractant receptors. Even topical application of LTB4 to human skin has been shown to promote the infiltration of neutrophils at the site of application; see "Production of Intraepidermal Microabscesses by Topical Application of Leukotriene B4", R. Camp, et al., Journal of Investigative Dermatology, 1984, 82, 202-207. This and all cited references are herein, incorporated by reference, in their entirety. LTB4 binds to receptors on the neutrophil surface and this initiates the formation of structures required for motility. Having attracted neutrophils in the blood to the site of inflammation, LTB4 induces adhesion of those neutrophils to the blood vessel endothelium. LTB4 increases the permeability of the blood vessels and following adhesion to the endothelium, neutrophils pass through the endothelium and into the stromal cell environment at the site of injury or infection. The neutrophils are directed by the chemotactic activity of LTB4, which means that the neutrophils move in the direction of increasing concentration of LTB4. At this point, the primary role of neutrophils is phagocytosis. Neutrophils adhere to and then engulf unwanted organisms and debris in the extracellular spaces of the inflamed tissue. By this time, the site of inflammation is infused with inflammatory exudate, an edemaous composition of pro-inflammatory products, metabolite and debris. Neutrophils use potent enzymes and noxious microbial agents to perform phagocytosis. In another of its important functions, LTB4 influences phagocytic neutrophils to release quantities of glucuronidase and lysozyme into the extracellular environment, where they have a beneficial role in breaking down the acute inflammatory exudate and damaged tissue.

Interleukin-1β

Other than LTB4, the present invention touches on the role played by Interleukin-1β(IL-1β), a pro-inflammatory cytokine. While LTB4 may play a role in inducing adhesion of neutrophils to the endothelium, IL-1β is directly responsible for adhesion of the polymorphonuclear leukocytes (PMN) to the endothelium. IL-1β induces the expression of adhesion molecules on the surface of the endothelial cells, a necessary occurrence if neutrophils are to pass out of the blood and into the affected tissue. IL-1β is naturally present in human skin and blocking or antagonizing the role of IL-1β in adhesion, is generally anti-inflammatory.

Acute Verse Chronic Inflammation

Acute and chronic inflammation are somewhat loosely defined in the literature, but it is useful to think of four situations based on the histological and clinical presentations. As such, acute inflammation is characterized by the presence of polymorphonuclear leukocytes (mainly phagocytic neutrophils) at the site of inflammation. However, acute inflammation may further be characterized as being in a resolving or persisting state, depending on the length of time since the initial attack. Chronic inflammation is different from acute inflammation. Chronic inflammation may occur as a second stage of the inflammatory response, after the failure of the acute process to completely resolve the situation, or it may occur with an acute phase. Chronic inflammation may be caused by a persistent infection, prolonged irritation, a cellular immune response, a defective acute inflammatory response, an autoimmune disorder, lifestyle, prolonged psychological stress, etc. Chronic inflammation is characterized by the presence of mononuclear cells (mostly phagocytic macrophages, but also lymphocytes, monocytes and plasma cells) at the site of inflammation, and, like acute inflammation, may be classified as resolving or persistent. Only relatively recently has medical science identified and appreciated the role of chronic tissue inflammation in many disease etiologies. It is important to note that as inflammation progresses, both acute and chronic processes may be occurring simultaneously in close proximity to each other.

Once they have infiltrated the site of inflammation, neutrophils guided by LTB4 exert primary control over the acute inflammatory response with phagocytosis being their primary activity. However, it should also be noted that activated neutrophils are a primary source of LTB4. Thus, the potential for an amplifying feedback loop exists in which LTB4 directs the recruitment and activation of neutrophils to a site of inflammation and those neutrophils produce and release more LTB4 which recruits more neutrophils. At a later point in the acute stage, relatively small numbers of macrophages and lymphocytes also infiltrate the site to aid in removal of tissue debris and damaged cells, but the histology is still characterized by neutrophils. If the acute stage is unable to resolve the disorder and return the organism to homeostasis, a cross over from acute to chronic inflammation may occur, when neutrophils that have infiltrated the site of inflammation send out a chemical signal that reduces further neutrophil recruitment and promotes mononuclear cell influx. Activated macrophages dominate the chronic stage of inflammation. They perform many of the same functions as neutrophils, like phagocytosis, but they may also have a more system-wide effect. Also, macrophages are capable of cell division and antigen presentation to lymphocytes. Macrophages direct the chronic inflammatory response and promote the healing stage by producing a variety of cytokines (including LTB4) and growth factors. For example, TGF-$\beta$ (transforming growth factor beta) is responsible for down-regulating the inflammatory function of macrophages, while also stimulating them to produce cytokines, growth factors and collagenases that support healing.

Resolving chronic inflammation requires the elimination of immune cells (macrophages and leukocytes) from the affected area. Leukocytes and macrophages tend to accumulate in a tissue compartment because of recruitment and/or local proliferation (cell division). Neutrophils, lymphocytes and macrophages are depleted from a tissue compartment by emigration and cell death. Under favorable conditions of inflammatory response, immune cells enter and exit the site of inflammation at rates that prevent their over-accumulation in the affected area. In contrast to resolving chronic inflammation, persisting chronic inflammation results when emigration and cell death do not keep up with recruitment and proliferation. Such an imbalance is a pathological condition and may generally occur when chemical signals that inhibit emigration and cell death are inappropriately produced. The mechanisms of this are not completely understood. Concerning neutrophils, one aspect seems to be that stromal cells and fibroblasts in the affected tissues may release stromal-cell-derived factor 1 (SDF-1), which is pro-retentive for neutrophils, and interferon-$\beta$ (INF-$\beta$), which is pro-survival for neutrophils. Concerning activated T-cells, assorted interleukins and type I interferons (INF-$\alpha$ and INF-$\beta$) inhibit apoptosis and therefore, contribute to persistence of inflammation. One result of this pathological accumulation of leukocytes is the continuous release of lysosomal enzymes through exocytosis. Both neutrophils and macrophages release quantities of collagen- and elastase-destroying enzymes into the extracellular environment, where they have a beneficial role in breaking down inflammatory exudate and damaged tissue. However, these enzymes do not discriminate and may also digest healthy tissues. If the quantities of these enzymes is excessive, significant damage to healthy tissue will occur. Furthermore, the phagocytic cells also release into the environment, reactive oxygen metabolites, which may also attack healthy tissue. This attack itself, becomes an initiator of inflammatory response, extending the inflammatory state for days, months or even years. Thus in chronic, especially persisting inflammation, tissues are damaged by the causative agent as well as by the inflammatory response to that agent. In fact, in persisting inflammation, the original causative agent may have long ago been neutralized.

There is an important distinction to be made here. Some treatments are anti-inflammatory because they neutralize one or more original causative agents. For example, an invading bacteria may cause inflammation. If an effective anti-bacterial treatment neutralizes the invading bacteria, the inflammation may subside. In this sense, the anti-bacterial treatment could be called anti-inflammatory. This is different from the focus of the present invention. For example, an invading bacteria may cause inflammation. Now say, the bacteria persists for a long time such that the inflammation becomes chronic persisting. Thereafter, the invading bacteria is finally neutralized by targeted anti-bacterial treatment, but the inflammation continues because of its persisting nature. At this stage, treatment targeted at inflammation is indicated. It was not enough to remove the original causative agent. Treatment targeted at the original causative agent may have no effect on resolving the persisting inflammation. The affected person needs something that enters into the inflammatory process and interacts with the inflammatory process. The present invention is concerned with treatments targeted at inflammation. By "targeted at inflammation", "targeted anti-inflammatory composition", "anti-inflammatory specific" or the like, we mean a composition, method or treatment that interacts directly with the inflammatory process, other than by neutralizing one or more original causative agents, as just described.

LTB4 has been implicated in a number of persisting inflammatory disorders of the skin and internal organs, including psoriasis, eczema, erythema, acne, pruritus, cystic fibrosis, rheumatoid arthritis, asthma, allergies, colitis and others. In all of these, elevated levels of LTB4 have been observed. Such conditions are generally referred to as LTB4-mediated disorders and their study has led to the development of various LTB4 inhibitors and antagonists for treatment of chronic inflammatory disorders. Antagonists are targeted in their effect, blocking LTB4 from performing specific functions. Inhibitors, on the other hand, block the formation of LTB4 from arachidonic acid. Therefore, inhibitors potentially affect all functions that rely on LTB4 and this may have undesirable consequences. Methods of LTB4 inhibition include inhibiting 5-lipoxygenase directly as well as blocking 5-lipoxygenase-activating protein, so that 5-lipoxygenase cannot translocate into the cell membrane. Either way, the cascade leading to the formation of LTA4 is interrupted and LTB4 is not produced. In contrast, antagonists block the action of LTB4 on one or more receptors on leukocytes and/or the endothelium. Often it may be preferable to control or influence some activities of LTB4 and not others. In those cases, inhibition of LTB4 production is contraindicated while antagonism of LTB4 is indicated. As an example, during a persisting inflammatory disorder with chronically elevated LTB4 levels, it may be desirable to interrupt the inflammatory process by interrupting LTB4-mediated chemotaxis and IL-1β mediated adhesion of neutrophils. However, for neutrophils already present at the site of inflammation, LTB4 could still trigger exocytosis and the release of quantities of glucuronidase and lysozyme into the extracellular environment, where they have a beneficial role in breaking down the acute inflammatory exudate and damaged tissue. In this way, the front end of the inflammatory process may be checked, while the back end is allowed to proceed and the affected area allowed to exit the inflammatory process. As the inflammatory process subsides, the processes of healing and repair take over. In the better resolving outcomes, termed "healing", the tissue structure remains in tact or can be regenerated by tissue cell proliferation. In the lesser resolving outcomes, termed "repair" or "organization", the damaged tissue is replaced by scar tissue via the body's normal repair process. If either healing or repair are to succeed, the inflammatory process has to be checked and the potential for further damage reduced or eliminated. In general, the effectiveness of any treatment of conditions that are characterized by persisting elevated levels of LTB4, is evaluated by the regression or prevention of the symptoms of the condition.

Mushrooms: Immuno-Enhancement Verses Immuno-Suppression

Mushrooms belong to the *Basidiomycota phylum* of the fungi kingdom. Whole mushrooms and mushroom extracts have been used for centuries for a host of reported effects. Methods of use include oral ingestion, subcutaneous injection and topical application. Like any biologically active substance, the specific effects of mushrooms depend on various factors, including, the exact species of mushroom, the portion of the mushroom used, the pre-processing of the mushroom, the method of administering, the area of the body targeted for treatment, the treatment regimen and so on.

Mushroom compositions (especially edible compositions) are often touted for their immune enhancing, and energy enhancing properties. It should be remembered that immuno-enhancement is pro-inflammatory and therefore compositions of this type are contrary to the anti-inflammatory compositions of the present invention. Furthermore, many different types of products, including mushroom compositions, make anti-ageing claims. But the oft-used phrase "anti-ageing" is non-specific and may convey different, even mutually exclusive meanings, depending on the initial condition of the person undergoing an anti-ageing treatment. So, on the one hand, pro-inflammation (immuno-enhancement) may be anti-ageing while on the other hand, anti-inflammation (immuno-suppression) may be anti-ageing. Consider a person who eats a balanced diet, exercises regularly, does not smoke or consume excessive alcohol, and does not receive harmful amounts of sun exposure. As this person progresses beyond middle age, immune system function (inflammatory response) eventually weakens, despite all due care. In this case, pro-inflammatory treatments could be viewed as "anti-ageing". Alternatively, consider a thirty year old who eats poorly, does not exercise, smokes daily, consumes more than six ounces of alcohol per day and works outdoors. At thirty, this person may have an undiminished inflammatory response, but because of constant external stimuli, that response may always be activated, i.e. chronic, leading to damage of healthy tissue. In this case, anti-inflammatory treatments should be considered anti-ageing. To summarize, "immuno-enhancement" implies pro-inflammatory, while "anti-ageing" could be pro- or anti-inflammatory.

This point was emphasized in an article entitled "Mycological Medicine" (January 2002 issue of Functional Foods & Nutraceuticals). The author noted, "As powerful immune modulators and potentiators, medicinal mushrooms are contraindicated for a number of autoimmune conditions such as systemic lupus erythematosus and collagen autoimmune disorders." Further highlighting this point, a peer review, appearing immediately after the article, stated, "It is clear that the use of the medicinal mushroom extracts has its place in the management of certain chronic conditions, including cancer. However, the author does point out that the use of such extracts is not advocated in certain conditions, such as autoimmune states. This is a well-founded warning because these extracts enhance the functioning of the inflammatory cells, and boosting the activity of such cells is not advisable when chronic inflammation forms part of the disease pathogenesis." Therefore, a composition, even if it claims to be anti-ageing does not necessarily have an anti-ageing effect on all persons treated with that composition. Furthermore, two compositions having one or more mushrooms in common, do not necessarily have the same general effect on all persons treated, even if both compositions claim to be anti-ageing. It depends how and on whom the compositions are used. It goes without saying, that compositions comprising extracts from taxonomically different mushrooms, do not generally behave the same way.

As noted, certain mushrooms can be used to enhance immune function. Again quoting from the article "Mycological Medicine", "Medicinal mushrooms' powerful immune-modulating and potentiating activity help support and enhance overall immune function. Researchers also are finding that mushrooms can directly stimulate both the basic (lymphocytes, neutrophils, etc.) and secondary immune responses (immunoglobulins IgE, IgA, IgG) of the immune system. This stimulus can increase production of immune defenders such as cytokines and macrophages, which play vital roles in recognizing and removing foreign antigens, as well as releasing chemical mediators including interleukin-1." Further quoting, "Substances that have been found to potentiate the immune system include beta-glucans, lentins, polysaccharides, polysaccharide-peptide complexes, triterpenoids, nucleosides and other secondary metabolites. Many of these bioactive substances, through their stimulatory effects on the immune system, are showing powerful antitumour, antimutagenic and anticancer activity." The points to note are that certain mushrooms are understood to increase cytokine production and stimulate neutrophil activity, i.e. certain mushrooms are capable of pro-inflammatory activity. Also, it is believed, at least in some cases, that the polysaccharides and glucans found in mushrooms stimulate the immune system, that is, are pro-inflammatory. The author explains, "Beta-glucan binds to macrophages and other phagocytic white blood cells at certain receptors and activates their anti-infection and antitumour activity by stimulating free radical production. This, in turn, signals the phagocytic immune cells to engulf and destroy foreign bodies, be they bacteria, viruses or tumor cells." Thus, many of the touted uses of mushroom extracts as anti-bacterial, anti-viral, anti-mutagenic, cardiovascular enhancing, etc. flow from the ability of mushrooms to address these conditions by stimulating the immune system and the inflammatory process. Finally, it must be remembered that polysaccharides and beta-glucans represent large classes of molecules. Nothing known in the field teaches or suggests that all polysaccharides or all beta-glucans are pro-inflammatory. The most that may be said is that some polysaccharides and beta-glucans are able to intervene in the inflammatory process.

Healthy skin, like all organs of the body and the body as whole, must maintain a state of homeostasis. Generally, homeostasis is disrupted by excess or deficiency, while the result is compromised skin integrity. Thus skin wrinkling and other signs of ageing skin can be a result of immuno weakness or hyper immuno activity (i.e. chronic inflammation). For example, in chronologically ageing people, the skin eventually thins and may be more easily damaged, while having a reduced ability to heal itself. As blood flow is diminished in older skin, so too is the immuno-response. Topical treatments that inhibit inflammation in the skin may be contraindicated for such people. On the other hand, eczema and psoriasis are hyper inflammatory disorders for which targeted anti-inflammatory compositions may be indicated.

Apart from the diminished capacities that accompany chronological ageing and autoimmune conditions, the human skin of any age is affected by exogenous or endogenous factors many of which are deteriorative. These factors include gravity, sun exposure, pollution, smoking, second hand smoke, pharmaceuticals, diet, trauma and others. Most of these factors (perhaps not gravity) are inflammatory to the skin and lead to deterioration of the collagen and elastin network in the surface layers of the skin. This deterioration leads to loss of skin elasticity and firmness, leading to sagging and wrinkling of the skin. Thus, even within the substantially younger population, there may occur changes in the skin which visibly manifest as wrinkles Generally, these visible manifestations are called "pre-mature ageing" of the skin.

The literature reports mushroom containing compositions that exhibit anti-inflammatory properties. WO2005/067955 claims that a topical poultice of *Fomitopsis officinalis* (common name: Agarikon) has long been used for anti-inflammation, and that in other forms, the mushroom is used to treat tuberculosis. The article is not specific about what types of inflammation the topical poultice may be effective in treating. Nor is it specific about how to make such poultices, even the concentration of Fomitopsis not being given. Which parts of the mushroom to use and how to prepare an extract for use in the poultice are not described. The reported components of this mushroom are beta glucans, triterpenoids, agaricin and antibiotics, but there is no explanation of how *Fomitopsis officinalis* intervenes, if at all, in the inflammatory process. Do the compositions mentioned neutralize the original causative agent of inflammation or are the compositions anti-inflammatory specific? It is not possible to know, because no compositions are disclosed.

Other known topical compositions of mushroom extract include the following, which are reported to treat or prevent ageing and wrinkling of the skin.

KR 2004084581 is entitled, Preservative Free Cosmetic Composition Containing The Extract of *Dictyophora Indusiata* To Prevent Skin Wrinkles, Wherein The Composition Displays High Antibacterial Effect And Is Thus Effective For Anti-Inflammation. Reported therein, is a preservative free cosmetic composition for the prevention of skin wrinkles containing an ethanolic extract of *Dictyophora Indusiata* mycelium. The extract concentration is 0.5-20% of the composition. Reportedly, the moisturizing composition displays high antibacterial effect and is thus effective for anti-inflammation. As the title itself explains, any anti-inflammatory activity of this composition comes from the composition's anti-bacterial activity. From the title and abstracts available, this can be understood to say that after the composition has neutralized invading bacteria, inflammation will subside. Nothing in the title or abstract suggest that the *Dictyophora Indusiata* extract directly intervenes in the inflammatory process. More specifically, nothing in the title and abstract suggest that *Dictyophora Indusiata* extract has any effect on LTB4 mediation of neutrophils. This is unlike compositions of the present invention which are anti-inflammatory specific and do influence the LTB4 mediation of neutrophils.

JP 11292785 describes a topical preparation containing one or more extracts of *Agaricus blazei* mushroom and the filtrate of the mycelium culture, combined with an active oxygen scavenger. The composition reportedly inhibits the damage of dermal fibroblast cells by ultraviolet rays; prevents the formation of peroxy lipid caused by active oxygen in the skin; is effective for the prevention and improvement of wrinkles or deterioration in skin elasticity; prevents and improves skin inflammation and roughening. The composition contains many active species other than the *Agaricus* mushroom, For example, active oxygen scavengers include: extracts of *Hamamelis, Quercus, Aesculus, Sanguisorba, Paeonia, Ginkgo bibloba L., Betulaceae* tree, parsley, carotenoid, flavonoid, tannin, superoxide dismutase, gallic acid and its salts or derivatives, hydroquinone, thioredoxin and thioredoxin reductase. JP 11228439 also describes a preparation comprising an extract of mycelia of *Agaricus blazei* (pref. at 0.0001-5 wt. %), at least one kind of physiologically active substance of animal origin (e.g. a placenta or spleen extract from mammal such as human or cattle, soluble eggshell membrane protein, basic or acidic fibroblast growth factor, epithelial cell growth factor, nucleic acid), 0.0001-3.0 wt. % of an anti-inflammatory agent, mucopolysaccharides (e.g. hyaluronic acid) and a 2-hydroxycarboxylic acid. Reportedly, the composition potentiates both a moisturizing effect and activates epidermal fibroblasts to treat skin aging symptoms. The reported role of *Agaricus* in these compositions is activation of dermal fibroblast cells, which is part of the healing and repair processes. Generally, the beta-glucans extracted from this mushroom species are reported to be used in cancer treatment where they aid in the production of interferon and interleukin (pro-inflammatory). Also, beta-glucans are known to stimulate macrophage activity (pro-inflammatory). Of course, those treatments are not generally topical. The point is that, the use of *Agaricus* in these references is not anti-inflammatory specific and even the presence of a separate anti-inflammatory ingredient in JP 11228439 indicates that the *Agaricus* is not targeted at inflammation. This is unlike compositions of the present invention wherein one or more mushroom extracts are anti-inflammatory specific and do influence the LTB4 mediation of neutrophils.

JP 63183537 reportedly describes an anti-inflammatory agent having low toxicity, containing an extract of *Heterobasidiae* (e.g. *Auricularia auricula-judae, A. polytricha, A. mesenterica,* etc.). The active ingredients of the extract are reported to be polysaccharides. The polysaccharides are xylose, mannose, glucuronic acid, etc., in the case of *Auricularia auricula-judae*. The extracted components of *Auricularia auricula-judae* are blended with various drug bases in liquid state, creamy state, etc., and used as an anti-inflammatory drug. The concentration of extract used is preferably 0.001-20.0 wt. %.

None of the foregoing references discloses, nor are the applicant's aware of prior art compositions comprising *Hypsizygus ulmarius* extract for use as a targeted LTB4 antagonist and/or IL-1β antagonist, in the skin. Nothing in the prior art suggests that *Hypsizygus ulmarius* extract could be effective for resolving persisting skin inflammation and thereby mitigating the effects of persisting inflammation, particularly visible signs of ageing, such as wrinkles. None of the foregoing discloses topical composition comprising an anti-inflammatory effective amount of *Hypsizygus ulmarius* extract, where the anti-inflammatory action is LTB4 antagonism and/or IL-1β antagonism.

OBJECTS OF THE INVENTION

A main object of the present invention is to provide topical compositions and methods that are effective for treating, inhibiting, preventing or reversing the effects of persisting inflammation.

Another object of the invention is to provide anti-inflammatory-specific compositions comprising *Hypsizygus ulmarius* extract.

Another object of the present invention is to provide topical compositions and methods that are effective for treating, inhibiting, preventing or reversing the visible signs of ageing skin, particularly wrinkles.

Another object of the invention is to provide topical compositions that function effectively as anti-chemotactic agents for LTB4, while not directly interrupting the arachidonic acid cascade.

Another object of the invention is to provide topical compositions that function effectively as anti-adhesion agents for IL-1β.

SUMMARY OF THE INVENTION

The present invention includes topical compositions of *Hypsizygus ulmarius* extract in amounts that are effective to influence LTB4-mediated chemotaxis and/or adhesion of polymorphonuclear leukocytes, as well as IL-1β mediated adhesion of polymorphonuclear leukocytes. The *hypsizygus ulmarius* extract may be used alone or in combination with secondary anti-inflammatory and skin active agents. The secondary anti-inflammatory agents may or may not function by antagonizing LTB4-mediated chemotaxis and IL-1β mediated adhesion. The extract may be incorporated into a cosmetically acceptable vehicle. The present invention includes methods of treating skin inflammation by applying to inflamed skin, anti-inflammatory effective amounts of *Hypsizygus ulmarius* extract. Preferably, compositions of the present invention are used to treat LTB4-mediated, persisting skin inflammation.

DETAILED DESCRIPTION OF THE INVENTION

Throughout this specification, the terms "comprise," "comprises," "comprising" and the like shall consistently mean that a collection of objects is not limited to those objects specifically recited.

*Hypsizygus ulmarius* (a.k.a. elm oyster, shirotamagitake) has the following taxonomical classification: kingdom: Fungi, phylum: *Basidiomycota*, class: *Basidiomycetes*, order: *Agaricales*, family: Tricholomataceae, genus: *Hypsizygus*. The *ulmarius* species should not be confused with other members of the *Hypsizygus* genus, namely *circinatus, elongatipes, ligustri, marmoreus* and *tessulatus*. Some older references may confuse "*ulmarius*" and "*tessulatus*", but more recently the differences between these species have been clarified.

Extracts of *Hypsizygus ulmarius* suitable for use in the present invention may be prepared from mushrooms harvested in wild or cultivated sites. Alternatively, and preferably, the extracts are prepared from mushrooms grown by tissue culture, under reproducible conditions. Cultures may be prepared by cloning methods or from spores. The quality and characteristics of extracts prepared from tissue culture can be reproduced with much greater reliability than by growing in the wild or even in a cultivated field. In the wild, *Hypsizygus ulmarius* may grow on maple boxelder maple trees from which the mushroom receives its nutrients, through its mycelium network buried in the tree trunk. It may be appreciated that there will be variation in the composition of wild *Hypsizygus ulmarius* mushrooms depending on the exact tree on which the mushroom grows, the age of the tree, the location on the tree, the amount of sunlight received by the tree, the season, time of day, etc. In contrast, the components of *Hypsizygus ulmarius* mushrooms by tissue culture are significantly more uniform, predictable and controllable. Therefore, *Hypsizygus ulmarius* mushrooms grown from tissue culture are preferred. Mushroom extracts produced in this way are commercially available from Fungi Perfecti® LLC, Olympia, Wa. 98507.

Extracts useful in the present invention are obtained with an ethanolic solvent. Generally, the greater the percent ethanol used for extraction the greater will be the percent recovery of lipid soluble materials, in this case complex carbohydrates. In terms of extract potency, the preferred solvent is an 80% or greater ethanolic solvent. However, where cost is a factor, suitable extracts may be obtained with 30% ethanolic solvent and possibly lower. Extracts may be obtained from the whole mushroom, but it is preferred to use the mycelium; the fine, root-like portion of the mushroom that exists within the substrate from which the mushroom grows. The mycelium absorbs nutrients from the substrate by secreting enzymes that break down nutrients for absorption. Therefore, the mycelium is a richer source of certain bioactive materials than is the fruit body of the mushroom. Extracts may be added to compositions of the present invention in liquid or solid form. Fungi Perfecti® distributes *Hypsizygus ulmarius* ethanolic extract in liquid or powdered form.

Example 1

Three *Hypsizygus ulmarius* 34% ethanolic extract samples received from Fungi Perfecti® underwent a composition analysis. Sample 1 was received from Fungi Perfecti® in powdered form and was not further treated. Sample 2 was received in powdered form having been subjected to 13-17 kiloGrays of gamma radiation. Both samples 1 and 2 were dried down at atmospheric pressure, from a 34% ethanolic extract, via Refractance Windows™ technology. Sample 3 was received from Fungi Perfecti® in liquid form and subsequently dried by the applicants into a powder, on a rotary evaporator operating at 40° C., for four hours. The drying was carried out at a negative pressure of about 1 atmosphere to lower the boiling point of the solvent and therefore, the temperature needed for drying. Lower drying temperatures are preferred to avoid the destructive effects of exposure to high heat, namely caramelizing of the sugar components of the extract.

Using HPLC-PAD, measurements of free mono- and oligosaccharides were made. Subsequently, the samples were subjected to acid hydrolysis with 10% hydrochloric acid solution for 2 hours at 100° C. Acid hydrolysis releases all monomer sugar units from oligo and polysaccharides. Thereafter, the total sugar content of the samples was measured. The results are shown in table 1.

TABLE 1

Saccharide composition of Fungi Perfecti ®
*Hypsizygus ulmarius* extracts

| Sample | % Galactose | % Glucose | % Oligosaccharide |
|---|---|---|---|
| before hydrolysis | | | |
| 1 | 12 | 18 | 18 |
| 2 | 11 | 18 | 18 |
| 3 | 7 | 15 | 19 |
| after hydrolysis | | | |
| 1 | 12 | 58 | — |
| 2 | 12 | 57 | — |
| 3 | 10 | 56 | — |

Sample 1 was further analyzed for protein content. Analysis was conducted before and after acid hydrolysis with 6N hydrochloric acid for 16 hours at 110° C. Table 2 shows the results.

TABLE 2

Protein composition of Fungi Perfecti ®
*Hypsizygus ulmarius* extract

| Sample | % free amino acid | % total amino acid | % protein |
|---|---|---|---|
| 1 | 2 | 10 | 8 |

Table 3 further breaks down and summarizes the data of tables 1 and 2. As shown, samples 1 and 2 have the same saccharide profile. Sample 3 is similar to samples 1 and 2, but has a lower percentage of free galactose and free glucose.

TABLE 3

Saccharide, protein composition of Fungi Perfecti ®
*Hypsizygus ulmarius* extracts

| Components | | Sample 1 dried via windows refractance, non-irradiated | Sample 2 dried via windows Refractance, irradiated | Sample 3 dried via rotary evaporator, non-irradiated |
|---|---|---|---|---|
| % galactose: | total | 12 | 12 | 10 |
| | free | 12 | 12 | 7 |
| % glucose: | total | 58 | 58 | 56 |
| | free | 18 | 18 | 15 |
| | oligosac. | 18 | 18 | 19 |
| | glycans, proteogly. | 22 | 22 | 22 |
| % free amino acid | | 2 | | |
| % protein | | 8 | | |
| % water | | 3 | | |
| % unidentified | | 17 | | |

Although the only difference between the test samples is the drying method and the use of gamma radiation, differences in the saccharide profiles are noted. Samples 1 and 2, dried by windows refractance, are 12% total galactose, all free, whereas the sample dried on the rotary evaporator is only 10% total galactose, only 7% of which is free. Similarly, samples 1 and 2 are 58% total glucose, of which 18% is free. This is compared to 56% total glucose for sample 3, of which 15% is free. Samples 1 and 2 have identical profiles for galactose and glucose, implying that gamma irradiation had no effect on the percent of those species.

Example 2

Anti-Chemotactic Effect On Neutrophils of *Hypsizygus Ulmarius* Extract Toward LTB4

Three test samples, identical to powder samples 1, 2 and 3 in Example 1, were assayed for their ability to inhibit neutrophil chemotaxis toward Leukotriene B4. The assay is designed to assess the ability of a material to inhibit the migration of polymorphonuclear leukocytes (PMN) toward a known chemotactic agent, LTB4. Heparinized peripheral venous blood (20-30 ml) was collected from healthy human donors (who had been requested to refrain from caffeine intake for the prior 12 hours), layered over a density gradient (mono-poly resolving media, ICN Pharmaceuticals, Costa Mesa, Calif.) and spun at 400×g for 30 min. The PMN rich fraction was removed and red blood cells (RBC) were lysed with hypotonic saline. The PMN were washed twice with Hank's Balanced Salt Solution (HBSS) and then resuspended in 5.0 ml HBSS with ions supplemented with 0.4% bovine serum albumin (Sigma). The concentration of cells was adjusted to 10×106 PMN/ml. Collected PMNs were greater than 95% pure and 98% viable as assessed by the trypan blue exclusion assay.

The assay was performed using the Boyden chamber apparatus with blind well chambers fitted with 5 μm pore size filters (Millipore). The apparatus consists of two vertical chambers separated by a filter that contains pores of a size chosen such that the holes are large enough for the cells to actively crawl through them but not so large that the cells can physically fall through into the lower chamber. PMN were then pre-incubated with the mushroom samples at 0.1% and 1% concentrations on a weight per volume basis. A 200 μl PMN cell suspension was layered on the top of the filter, and 100 μl chemotactic factors were added to the lower compartment. The chemoattractant used in the present experiment was 0.125 nM LTB4. Following incubation at 37° C. for 90 min., under a humidified atmosphere with 5% CO2, the filters were fixed with propanol and stained with haematoxylin and eosin. The PMN chemotactic response was determined by the distance to the leading front and the number of cells that migrated to the front. The distance to the leading front was determined at 400× magnification by the distance the majority of the cells migrated through the filter. The results were expressed as the average number of cells per high powered field at the leading (migratory) front (PMN/HPF). In this assay, 0.5% caffeine was used as a positive control. A negative control, with no anti-chemotactic agent, was also used. The results, shown in Table 4, are the percent reduction in chemotactic activity compared to the negative control.

TABLE 4

Percent reduction in chemotactic activity compared to the negative control

| concentration (w/v) | positive control (caffeine) | Sample 1 dried via windows refractance, non-irradiated | Sample 2 dried via windows refractance, irradiated | Sample 3 dried via rotary evaporator, non-irradiated |
|---|---|---|---|---|
| 0.1% | | not significant | not significant | 42% |
| 0.5% | 96% | | | |
| 1.0% | | 39% | not significant | 48% |

The *Hypsizygus ulmarius* ethanolic extract dried on the rotary evaporator displays significant anti-chemotactic activity on neutrophils toward LTB4. Significant activity is present at both concentrations. Thus, at concentrations of at least 0.1% (w/v), significant anti-chemotactic activity of *Hypsizygus ulmarius* 34% ethanolic extract is established. The *Hypsizygus ulmarius* ethanolic extracts dried via windows refractance performed differently. The non-irradiated sample was not effective at 0.1% concentration, but did display significant (39%) activity at 1% (w/v) concentration (although lower activity than the rotary dried sample). The irradiated sample did not display significant anti-chemotactic activity at either concentration. It may be concluded that a Refractance Windows™ drying procedure diminishes the anti-chemotactic activity of *Hypsizygus ulmarius* extract compared to the rotary evaporative drying described herein. It may also be concluded that gamma irradiation strongly diminishes the anti-chemotactic activity of *Hypsizygus ulmarius* extract, regardless of which drying method is used. Based on these results, *Hypsizygus ulmarius* extract useful in the present invention should not be gamma irradiated to the extent that all anti-chemotactic activity is lost. Furthermore, a preferred *Hypsizygus ulmarius* powdered extract is dried on a rotary evaporator, although samples prepared by windows refractance may also be used effectively.

Example 3

Anti-Chemotactic Effect On Neutrophils of *Hypsizygus Ulmarius* Extract Toward LTB4

At another time, the identical assay described in example 2 was performed on samples of *Hypsizygus ulmarius* 34% ethanolic extract (from Fungi Perfecti), in solution at concentrations of 0.1% and 1.0%, on a volume per volume basis (in contrast with the weight per volume basis above). The results were dramatically different. No anti-chemotactic effect was observed at either concentration.

Example 4

Anti-Chemotactic Effect On Neutrophils of Three Mushroom Extracts Toward LTB4

Three ethanolic mushroom extracts from Fungi Perfecti® were assayed for the ability to inhibit neutrophil chemotaxis toward Leukotriene B4. The samples assayed were ethanol extracts of *Fomitopsis officinalis, Ganoderma tsugae* and *Hypiszygus ulmarius*. The test sample of *Hypiszygus ulmarius* extract was equivalent to sample 3 in examples 1 and 2 above (34% ethanol and dried on a rotary evaporator, not gamma irradiated). The *Fomitopsis* and *Ganoderma* samples were received from Fungi Perfecti® in liquid form and dried on rotary evaporator in the manner described above. The assay was performed as described in example 2. It was found that *Hypsizygus ulmarius* and *Fomitopsis officinalis* extracts exhibit significant anti-chemotactic activity. In this trial, the percent reduction in chemotaxis due to 0.1% (w/v) *Hypsizygus ulmarius* extract was not significantly different from the negative control. The *Ganoderma tsugae* extract provided no statistically significant reduction of PMN chemotaxis. In this assay, 0.1% caffeine, the positive control, inhibited chemotaxis to 0.125 nM LTB4 by 93%. The results are shown in table 5.

TABLE 5

| | Percent reduction in chemotactic activity compared to negative control | | | |
|---|---|---|---|---|
| concentration (w/v) | positive control (caffeine) | Sample 1 *Fomitopsis officinalis* | Sample 2 *Ganoderma tsugae* | Sample 3 *Hypsizygus ulmarius* |
| 0.1% | 93% | 41% | not significant | not significant |
| 1.0% | | 93% | not significant | 72% |

The results of examples 2, 3 and 4 (tables 4 and 5) demonstrate the anti-chemotactic effect of *Hypsizygus ulmarius* extract at the concentrations shown. In examples 2 and 4, the percent reduction in LTB4-mediated chemotaxis is a comparison to the performance of the negative control sample, but also depends on the test conditions, for example, the concentration of neutrophils used in the test, the amount of LTB4 used to attract the neutrophils, environmental conditions, etc. For this reason, the percent reduction numbers are only meaningful when comparing them to one another in the same test. It is reasonably expected that concentrations of *Hypsizygus ulmarius* extract above 1% (w/v) will yield even greater anti-chemotactic activity. Greater reductions in LTB4-mediated neutrophil chemotaxis may be expected up to at least 20% (w/v) concentration before reaching 100% effectiveness.

Example 5

Effect of Three Mushroom Extracts on IL-1β Mediated Adhesion of Neutrophils

Three samples identical to those in example 4 were tested for their ability to inhibit endothelial adhesion of neutrophils by interfering with the effects of IL-1β. These samples were tested at final concentrations of 0.1% and 1% (w/v). Neutrophil adhesion was inhibited dose dependently with all samples tested. Adhesion of PMN to human dermal microvascular cells is a required step in the recruitment of leukocytes into the site of infection or irritation and was modeled for this assay in the following manner. Heparinized peripheral venous blood (20-30 ml) was collected from healthy human donors (who had been requested to refrain from caffeine intake for the prior 12 hours), layered over a density gradient (mono-poly resolving media, ICN Pharmaceuticals, Costa Mesa, Calif.) and spun at 400×g for 30 min. The PMN rich fraction was removed and RBC were lysed with hypotonic saline. The PMN were washed twice with Hank's balanced salt solution (HBSS) and then resuspended in 5.0 ml HBSS with ions supplemented with 0.4% bovine serum albumin (Sigma). The concentration of cells was adjusted to 10×106 PMN/ml. Collected PMNs were greater than 95% pure and 98% viable as assessed by the trypan blue exclusion assay.

Human dermal microvascular endothelial cells (HDMEC) were obtained from the Clonetics Corp (MD) and maintained according to specifications until confluent. PMN were incubated for 30 minutes with the test material before being placed on the endothelial cells. In preliminary experiments the optimum concentrations of stimulatory agents (IL-1β, 10 U/ml and TPA, 5 ng/ml) were determined. After incubation (30 min) with the test material plus tetradecanoyl phorbol acetate (TPA, 5 ng/ml) or with test material alone, with TPA alone or vehicle, PMN (350,000/well) were added to wells of a 96-well microtiter plate in which endothelial cells had been allowed to reach confluence. Endothelial cells had been pre-incubated with IL-1β (10 U/ml) for 60 min at 37° C. in 5% $CO_2$. After the two cell types had been in contact for two hours the supernatant was removed, remaining cells gently rinsed, and 100 µl of 0.25% rose bengal (ICN) stain in PBS was added for 5 min at room temperature. Non-adherent cells were removed by two subsequent washes (Medium 199 with 25 mM HEPES and 10% fetal bovine serum). Stain incorporated into cells was released by the addition of 200 µl of ethanol:PBS (1:1). After 30-45 min, the wells were read in an ELISA reader (Bio-Tek Instruments Inc, Winooslei, Vt., USA) at 570 nm. The level of adherence was given as the mean optical density (OD) reading at an $OD_{570}$ for wells containing endothelial cells plus PMN minus the mean $OD_{570}$ of wells containing endothelial cells alone.

Results of this assay (see table 6) indicate that the three mushroom samples all posses significant dose-dependent anti-adhesive properties. It can be appreciated that *Ganoderma tsugae* extract is less active than the other two mushroom extracts. In this assay, 1% caffeine (positive control), reduced PMN adhesion by 64%. Thus, at concentrations of at least 0.1% (w/v), significant anti-adhesion activity of 34% ethanolic extract of *Hypsizygus ulmarius* is established, while at concentrations of at least 1% (w/v) *Hypsizygus ulmarius* was as effective as the caffeine control (63%). Here again, the percent reduction numbers may only be meaningfully compared to other numbers within the same test. Nevertheless, the trend in table 6 indicates that concentrations at least as high as 10% (w/v) would increase the anti-adhesion effectiveness of all three extracts tested.

TABLE 6

Percent reduction in adhesion activity compared to negative control

| concentration (w/v) | positive control (caffeine) | Sample 1 *Fomitopsis officinalis* | Sample 2 *Ganoderma tsugae* | Sample 3 *Hypsizygus ulmarius* |
|---|---|---|---|---|
| 0.1% | | 34% | 30% | 35% |
| 1.0% | 64% | 63% | 50% | 63% |

Example 6

Anti-Chemotactic Effect On Neutrophils of an Algae And Corn Starch Toward LTB4

A 1% algae solution available under the trade name Polysea PF, supplied by Frutarom Industries, Ltd, and pure corn starch were assayed according to the method described above for anti-chemotactic activity of LTB4-mediated neutrophil chemotaxis. The samples were tested at concentrations of 0.1% and 0.5%. Polysea PF from *Frutarom* was assayed in liquid form. Caffeine at 0.1% was used as a positive control. A negative control was also used. Polysea PF has a significant anti-chemotactic activity, while corn starch has none. The corn starch result demonstrates that not all polysaccharides exhibit anti-chemotactic behavior. The results are shown in table 7.

TABLE 7

Percent reduction in chemotactic activity compared to negative control

| concentration | positive control (caffeine) | Polysea PF | corn starch |
|---|---|---|---|
| 0.1% | | 57% | no activity |
| 0.5% | 94% | 84% | no activity |

Examples 1-6 demonstrate several things. Firstly, pretreatment methods may have an effect on the composition of *Hypsizygus ulmarius* extract. The effect may be sufficient to alter the anti-inflammatory capacity of the extract.

Secondly, regarding anti-chemotaxis and anti-adhesion, not all mushroom extracts behave alike. Therefore, taxonomically different mushrooms should not be expected to perform the same way when used as anti-inflammatory treatments.

Thirdly, the anti-inflammatory performance of *Hypsizygus ulmarius* extract is quite sensitive to its carbohydrate composition. The composition of many mushroom extracts may not seem very sophisticated, being mostly an assortment of saccharides. However, even a slight difference in saccharide profiles was shown to alter the anti-inflammatory properties of *Hypsizygus ulmarius* extract. Also, pure corn starch, a polymer of glucose, had no anti-chemotactic or anti-adhesive effect, yet β-glucans (also polymers of glucose) are known to manifest wide ranging effects in the inflammatory process. It may reasonably be assumed that the inflammatory properties of many, if not most mushroom extracts, are sensitive to the exact saccharide composition of the extracts. This sensitivity of anti-inflammatory activity to carbohydrate composition of the *Hypsizygus ulmarius* extract even extends to the solvent used in obtaining the extract. Based on a knowledge of basic solubility behavior, we expect that water extracts of *Hypsizygus ulmarius* will have some anti-inflammatory activity, although commercial exploitation may not be worthwhile. However, ethanolic extracts of increasing solvent concentration withdraw from the mushroom, increasingly complex carbohydrates. In general, the complex carbohydrates impart a greater anti-inflammatory benefit than the simple carbohydrates. Therefore, when formulating compositions according to the present invention, the concentration of *Hypsizygus ulmarius* extract in the composition and the concentration of ethanolic solvent used to gather the extract may be considered.

As noted, the inflammatory properties of many, if not most mushroom extracts, are sensitive to the exact saccharide composition of the extracts. Therefore, the results of the above examples demonstrate that the behavior of one mushroom extract cannot be assumed from the behavior of another extract. Thus, it may be beneficial to have a number of different mushrooms in a single composition. Having several mushrooms in a single composition may extend the spectrum of coverage or allow more specific targeting of conditions and potencies.

Effective Amounts

The anti-chemotactic and anti-adhesion data strongly indicate that concentrations of *Hypsizygus ulmarius* powder, obtained from a 34% ethanolic extract according to the process described above, at least as low as 0.1% (w/v) and up to about 20% (w/v), are "anti-inflammatory effective". Examples 1, 2 and 4-6 use *Hypsizygus ulmarius* extract in powder form. It is also possible to use the extract in liquid form, as in example 3. For a 34% ethanolic extract, it has been determined that the liquid form used at a concentration of 2.5% (v/v) is equivalent to the powder form used at a concentration of 0.1% (w/v). This ratio was determined simply by drying completely, a liquid extract and comparing the weight and volumes before and after. Therefore, we can expect a 34% ethanolic liquid extract at concentrations at least as low as 2.5% (v/v) to be anti-inflammatory effective. Similarly, a concentration of 25% (v/v) is equivalent to the powder form used at a concentration of 1.0% (w/v). What example 3 showed, is that concentrations of 1% (v/v) (or 0.04% w/v) and lower do not exhibit anti-inflammatory activities in the assays described. Therefore, a lower limit of effectiveness is noted between 0.04% and 0.1% (w/v) for 34% ethanolic extract. Furthermore, the anti-chemotactic and anti-adhesion data strongly indicate that the anti-inflammatory activity of 34% *Hypsizygus ulmarius* powder, obtained according to the process described above, continues to increase at least up to 20% (w/v). However, as noted, effective anti-inflammatory compositions may employ *Hypsizygus ulmarius* extracts obtained with levels of ethanolic solvent different from 34%. In fact, any level higher than 34% may be employed to make a composition according to the present invention. In general, extracts obtained with higher concentrations of solvent will be of a better quality as pertains to the anti-inflammatory activity, herein described. Therefore, the level of ethanolic extract used in topical anti-inflammatory composition will depend on the concentration of ethanol used in the extraction. We use 34% ethanolic extract as a standard and define a "34%-equivalent concentration" as that concentration of ethanolic extract that displays the same anti-inflammatory behavior as a given concentration of 34% ethanolic extract. For example, an 85% ethanolic extract is expected to have greater anti-inflammatory activity than a 34% extract, and therefore should require a smaller concentration to achieve the same effect. Given this definition, "anti-inflammatory effective concentration" or the like means from 0.1% (w/v) to about 20% (w/v) of a 34% ethanolic extract or a 34%-equivalent concentration, thereof. A 34%-equivalent concentration of *Hypsizygus ulmarius* extract can be determined by a person skilled in the art, through routine trial and error.

If incorporated into cosmetic vehicles having high alcohol content, caution should be taken to avoid precipitation of the ethanolic extract. Processing with high heat and radiation should be avoided to avoid degradation of the extract and loss of anti-chemotactic and anti-adhesion activity. Other than those restraints, the *Hypsizygus* extract described herein may be incorporated into any cosmetically or dermatologically acceptable vehicle intended for topical application. Such vehicles include solids, liquids, creams, lotions, emulsions, gels, serums, ointments, poultices, powders, bars, etc. Compositions may be packaged in any sort of cosmetic and dermatological package type and package material that does not adversely react with the composition. It may be advantageous to package compositions of the present invention in opaque or radiation resistant packaging to ensure the activity of the active ingredients. Compositions may be topically administered by any suitable methods including towelette, pump spray, aerosol spray, lotion pump, squeeze tube, lathering bar, etc.

Other Anti- and Pro-Inflammatory Agents

The present invention may comprise anti-inflammatory agents other than *Hypsizygus ulmarius* extract. One or more of these agents may work by influencing LTB4-mediated chemotaxis or IL-1β mediated adhesion. This may be preferable if no other anti-inflammatory effects are desirable or if one wishes to further manipulate the percent reduction of LTB4-mediated chemotaxis or IL-1β mediated adhesion. Alternatively, it may be desirable to use anti-inflammatory agents that have activity different from that of *Hypsizygus ulmarius* extract, thus providing a broader spectrum anti-inflammatory treatment. It is also possible to use agents that produce an anti-inflammatory synergistic effect with *Hypsizygus ulmarius* extract. Suitable anti-inflammatory agents may include any that are known by a person of ordinary skill in the art to be effective when used topically. This includes other mushroom extracts, either from species different from *Hypsizygus ulmarius* or extracts of *Hypsizygus ulmarius* obtained by extraction methods different from that described herein. Examples of mushrooms known or reported to have anti-inflammatory properties when topically applied include *Fomitopsis officinalis* (a.k.a. Agaricon), *Cordyceps sinensis, Inontus obliquus* (a.k.a. Chaga), *Phellinus linetus* (a.k.a. Mesima), *Piptoporus betulinus* (a.k.a. Birch Polypore), *Agaricus blazei, Dictyophora indusiata* and *Auricularia auricular-judae*.

The present invention may even comprise pro-inflammatory agents. Pro-inflammatory agents may be used to manipulate the percent reduction of LTB4-mediated chemotaxis or IL-1β mediated adhesion caused by *Hypsizygus Ulmarius* extract. For example, agents that are chemo-attractants for blood neutrophils (pro-inflammatory) could be used in conjunction with *Hypsizygus Ulmarius* extract to more finely adjust the numbers of neutrophils recruited to a site of inflammation. Suitable pro-inflammatory agents may include any that are known by a person of ordinary skill in the art to be effective when used topically. This includes mushroom extracts. One example of mushroom extract reported to have pro-inflammatory properties is the hot water extract of *Ganoderma lucidum* (a.k.a. Reishi, Ling-Zhi). The specific polysaccharides present in the hot water extract of *Ganoderma lucidum* have been shown to by a potent chemoattractant for neutrophils and an effective inhibitor of neutrophil apoptosis. (See "Signaling Mechanisms Of Enhanced Neutrophil Phagocytosis And Chemotaxis By The Polysaccharide Purified From *Ganoderma Lucidum*", Hsu, et al. British Journal of Pharmacology, 2003, 139, p. 289-298) We note that in other places *Ganoderma lucidum* has been reported to have anti-inflammatory properties, even when used topically (see, for example, Botanicals: A Phytocosmetic Desk Reference, Frank S. D'Amelio, Sr., 1999, p. 181) but this study definitively establishes the hot water extract as pro-inflammatory via enhanced chemotaxis.

The following examples demonstrate that the anti-inflammatory benefits of *Hypsizygus ulmarius* may be finely tuned (enhanced or mitigated) by the inclusion of natural extracts of various sorts.

Example 7

Anti-Chemotactic Effect on Neutrophils of Three Combinations Of Actives Toward LTB4

Three combinations of actives were tested for their ability to inhibit neutrophil chemotaxis toward LTB4. All three combinations included *Hypsizygus ulmarius* extract. The components of the three samples are shown in table 8. The positive control in this study was caffeine at 0.5% concentration. The results are shown in table 9.

TABLE 8

| Component | Sample 1 | Sample 2 | Sample 3 |
|---|---|---|---|
| *Hypsizygus ulmarius* 34% liquid extract (v/v) | 2.5% | 2.5% | 2.5% |
| *Cordyceps sinensis* 7% powder extract | | 0.01% | 0.01% |
| *Ganoderma lucidum* 10% powder extract | | 0.01% | 0.01% |
| [1]Pronalen Sensitive Skin | 0.01% | | |
| [2]Crodarom Ginger Special | 0.01% | | |
| [3]Tetrahydrocurcuminoids | 0.001% | | |

[1]butylene glycol/water/*ocimum sanctum* leaf extract/*silybum marianum* fruit extract, available from Centerchem, Inc.
[2]butylene glycol/purified water/*zingiber officinale* root extract/Polysorbate 20, available from Croda USA.
[3]*curcuma longa* (turmeric) root extract.

TABLE 9

| Percent reduction in chemotactic activity compared to negative control | | | |
|---|---|---|---|
| positive control (caffeine) | Sample 1 | Sample 2 | Sample 3 |
| 97% | 80% | 71% | 59% |

Example 8

IL-1β Mediated Anti-Adhesion Effect of Three Combinations of Actives

The same three combinations of actives in example 7 were tested for their ability to inhibit IL-1β mediated adhesion of neutrophils. The positive control in this study was caffeine at 1.0% concentration. The results were as follows.

TABLE 10

| Percent reduction in adhesion activity compared to negative control | | | |
|---|---|---|---|
| positive control (caffeine) | Sample 1 | Sample 2 | Sample 3 |
| 47% | 44% | not significant | 47% |

Discussion of Examples 7 and 8.

Referring to table 9, all three combinations of actives are effective at reducing the chemotaxis of neutrophils toward LTB4. However, the presence of both *Cordyceps sinensis* and *Ganoderma lucidum* in sample 2, seems to provide better anti-chemotactic activity than *Hypsizygus ulmarius*, by itself. At first, this may seem surprising, given that *Ganoderma lucidum* was reported above to be pro-inflammatory. However, we also noted above, that the hot water extract of *Ganoderma lucidum* is a potent chemoattractant for neutrophils. Therefore, while not wishing to be bound by any one theory, it may be that the *Ganoderma lucidum* extract in the Boyden chamber is competing against LTB4 for neutrophils. If this is the case, then fewer neutrophils are migrating toward LTB4 in the Boyden chamber, not because of antagonism or inhibition of LTB4, but because the neutrophils were exposed to a second chemoattractant.

Referring to table 10, the presence of *Cordyceps sinensis* and *Ganoderma lucidum* appear to mitigate the anti-adhesion effects provided by *Hypsizygus ulmarius*. Again, it may be that *Ganoderma lucidum* is, as recently reported, pro-inflammatory, this time pro-adhesion.

Regarding the other components of test sample 1, *Ocimum sanctum* (Holy Basil) leaf extract has many reported properties and is generally considered anti-inflammatory. *Silybum marianum* (Lady's thistle) extract is generally regarded as anti-inflammatory and Turmeric root extract is widely regarded as anti-inflammatory. Ginger is reported to have anti-inflammatory or pro-inflammatory properties, perhaps depending on the method of use. It has many medicinal uses. In one sense it is considered pro-inflammatory, known to have vasodilatory effects that increase blood flow and produce warming sensation, when applied topically. Alternatively, it is considered anti-inflammatory, used topically to relieve the pain of arthritis. It is also reported to stimulate hair follicles when used topically.

Thus, depending on the relative amount of anti-inflammatory and pro-inflammatory agents employed, a composition comprising *Hypsizygus ulmarius* extract may be strongly anti-inflammatory, strongly pro-inflammatory or moderately or weakly either. In either case, the present invention only requires that *Hypsizygus ulmarius* extract is responsible for at least some anti-inflammatory activity in the use of the composition. In other words, other agents in the composition may not completely mitigate the anti-inflammatory activity of the *Hypsizygus ulmarius* extract. Therefore, preferred topical compositions of *Hypsizygus ulmarius* extract are overall, anti-inflammatory.

A wide range of cosmetically and pharmaceutically acceptable materials may be advantageously used to preserve or alter the physical properties of the composition in order to create for the user a unique and pleasurable sensorial experience. For example, without departing form the spirit of the invention, an effective amount of one or more of the following may be included: abrasives, absorbents, anti-caking agents, antifoaming agents, antifungal agents, antimicrobial agents, antioxidants, binders, biocides, buffers, bulking agents, colorants, corrosion inhibitors, deodorants, film formers, fragrance, humectants, opacifiers, oxidizers, pH adjusters, plasticizers, preservatives, propellants, reducing agents, slip modifiers, solvents, stabilizers, surfactants, viscosity controlling agents. In addition, a wide range of cosmetically and pharmaceutically acceptable materials and actives may be used to provide a benefit to the skin. These include an effective amount of one or more of the following: abrasives, absorbents, antiacne agents, anti-ageing agents, antifungal agents, anti-inflammatories, antimicrobial agents, antioxidants, antiperspirants, astringents, biocides, chemical exfoliants, cleansers, deodorants, depilating agents, epilating agents, external analgesics, humectants, make-up removers, skin bleaching agents, skin conditioning agents, skin protectants, sunscreens, tanning agents and UV absorbers. Just about any cosmetic, dermatologic or pharmaceutic agent suitable for topical use, is within the purview of this invention, the only requirement being that the overall composition must function effectively as anti-chemotactic and anti-adhesion agents for LTB4.

Inflammatory conditions of the skin or conditions having an inflammatory component, which may be treated with compositions according to the present invention include: Acne, Actinic keratosis, Angioma, Athlete's foot, Aquagenic pruritus, Atopic dermatitis, Baldness, Basal cell carcinoma, Bed sore, Behcet's Disease, Blepharitis, Boil, Bowen's Disease, Bullous pemphigoid, Canker sore, Carbuncles, Cellulitis, Chloracne, Chronic dermatitis of the hands and feet, Dyshidrosis, Cold sores, Contact dermatitis, Creeping eruption, Dermatitis, Dermatitis herpetiformis, Dermatofibroma, Eczema, Epidermolysis bullosa, Erysipelas, Erythroderma, Friction blister, Genital wart, Hidradenitis suppurativa, Hives, Hyperhidrosis, Ichthyosis, Impetigo, Jock itch, Kaposi's sarcoma, Keloid, Keratoacanthoma, Keratosis pilaris, Lice infection, Lichen planus, Lichen simplex chronicus, Lipoma, Lymphadenitis, Malignant melanoma, Melasma, Miliaria, Molluscum contagiosum, Nummular dermatitis, Paget's disease of the nipple, Pediculosis, Pemphigus, Perioral dermatitis, Photoallergy, Photosensitivity, Pityriasis rosea, Pityriasis rubra pilaris, Psoriasis, Raynaud's disease, Ring worm, Rosacea, Scabies, Scleroderma, Sebaceous cyst, Seborrheic keratosis, Seborrhoeic dermatitis, Shingles, Skin cancer, Skin Tags, Spider veins, Squamous cell carcinoma, Stasis dermatitis, Tick bite, Tinea barbae, Tinea capitis, Tinea corporis, Tinea cruris, Tinea pedis, Tinea unguium, Tinea versicolor, Tinea, Tungiasis, Vitiligo and Warts Compositions according to the present invention are suitable for and effective when used topically. Because the skin is virtually always subject to assault from the environment, the signs of ageing due to persisting inflammation are best addressed by periodic application over the long term. For example, to prevent, mitigate or reverse the signs of ageing due to persisting inflammation, the skin should be treated at least three times per week, preferably daily, most preferably, twice per day. Preferably, on any given day, a treatment is administered prior to exposure to the harshest skin inflammatory agents. For most people, this will be shortly after sleeping, during which time the skin is least under assault from external factors. For most people, this may be in the morning, before leaving the house. By treating the skin prior to exposure to inflammatory agents, the inflammatory process may be interrupted before significantly progressing. It should also be advantageous to apply a composition according to the present invention shortly before sleep. As the body is resting, it is least under attack from external factors and best able to affect repairs to the skin. Therefore, by applying a composition according to the present invention shortly before sleep, the benefits provided by the *Hypsizygus ulmarius* extract will be increased. In this case, treatment is used to address the pro-inflammatory effects of exposure to various environmental factors. Compositions according to the present invention should be applied to areas of the skin where protection is desired or to areas of the skin where signs of ageing are already visible. The composition may be spread over the target area and allowed to remain on the skin for a substantial period of time, say, at least five minutes, preferably up to one hour, most preferably, more than one hour. The substantial period of time is needed to allow the active components of the extract to penetrate the outermost layers of the skin. Because of this, rinsing the skin with water or alcohol, or otherwise cleansing the treated skin, should be avoided for the substantial period of time. The amount of product applied is preferably, at least about 2.0 mg per squared centimeter. More preferably, the amount applied by any given individual will be arrived at by trial and error. Having used a composition according to the present invention, a user may adjust the amount of composition applied based on the results observed.

The *Hypsizygus ulmarius* ethanolic extract described herein may be incorporated into any cosmetically or dermatologically acceptable vehicle intended for topical application. Having regard for the alcoholic nature of the extract, such incorporation may be affected by generally known methods of cosmetic and dermatologic science. Methods of the sort are generally described in, for example, Poucher's Perfumes, Cosmetics and Soaps (vol. 3, 9$^{th}$ edition, Chapman & Hall) or Remington's Pharmaceutical Sciences (18$^{th}$ edition, Mack Publishing).

The compositions disclosed herein, are effective for treating, inhibiting, preventing or reversing the effects of persisting inflammation, as well as for treating, inhibiting, preventing or reversing the visible signs of ageing skin, particularly wrinkles. The topical compositions described function effectively as anti-chemotactic agents for LTB4, while not directly interrupting the arachidonic acid cascade. The compositions also function effectively as anti-adhesion agents for IL-1β.

That which is claimed is:

1. A method of treating persisting skin inflammation comprising the step of applying to inflamed skin a topical anti-inflammatory-specific composition comprising an anti-inflammatory effective amount of *Hypsizygus ulmarius* ethanolic extract.

2. A method of treating visible signs of skin ageing caused by skin inflammation comprising applying to visibly aged skin a topical anti-inflammatory-specific composition comprising an anti-inflammatory effective amount of *Hypsizygus ulmarius* ethanolic mycelium extract.

3. The method of claim 2 wherein the composition is applied to the skin at least three times per week.

4. The method of claim 3 wherein the composition is applied to the skin daily.

5. The method of claim 4 wherein the composition is applied to the skin at least twice per day.

6. The method of claim 1 wherein the composition is applied to the skin shortly after waking.

7. The method of claim 1 wherein the composition is applied to the skin shortly before sleep.

8. A method of treating persisting skin inflammation comprising the step of applying to inflamed skin a topical anti-inflammatory-specific composition comprising:
an anti-inflammatory effective amount of *Hypsizygus ulmarius* ethanolic extract;
ganoderma lucidum extract and/or Cordyces sinensis extract; and one or more of Ocimum sanctum leaf extract, Silybum marianum fruit extract, ginger root extract and turmeric root extract.

* * * * *